(12) United States Patent
Wagner et al.

(10) Patent No.: US 8,362,185 B2
(45) Date of Patent: Jan. 29, 2013

(54) POLYAMMONIUM/POLYSILOXANE COPOLYMERS

(75) Inventors: Roland Wagner, Siegburg (DE); Horst Lange, Bochum (DE); Anita Witossek, Langenfeld (DE); Karl-Heinz Stachulla, Leverkusen (DE); Karl-Heinz Sockel, Leverkusen (DE); Martin Kropfgans, Odenthal (DE)

(73) Assignee: Momentive Performance Materials GmbH, Leverkusen (DE)

( * ) Notice: Subject to any disclaimer, the term of this patent is extended or adjusted under 35 U.S.C. 154(b) by 1185 days.

(21) Appl. No.: 11/997,620

(22) PCT Filed: Jul. 31, 2006

(86) PCT No.: PCT/EP2006/064833
§ 371 (c)(1), (2), (4) Date: Jun. 26, 2008

(87) PCT Pub. No.: WO2007/014930
PCT Pub. Date: Feb. 8, 2007

(65) Prior Publication Data
US 2009/0142293 A1    Jun. 4, 2009

(30) Foreign Application Priority Data
Aug. 1, 2005   (DE) .................. 10 2005 036 602

(51) Int. Cl.
*C08G 77/54* (2006.01)

(52) U.S. Cl. ............... 528/20; 528/21; 528/24; 528/28; 528/33

(58) Field of Classification Search ............ None
See application file for complete search history.

(56) References Cited

U.S. PATENT DOCUMENTS

| | | | |
|---|---|---|---|
| 3,402,191 A | 9/1968 | Morehouse | |
| 4,478,893 A | 10/1984 | Schonfelder et al. | |
| 6,835,419 B2 | 12/2004 | Herzig et al. | |
| 7,319,120 B2 | 1/2008 | Herzig et al. | |
| 7,329,707 B2 | 2/2008 | Sandner et al. | |
| 7,563,856 B2 * | 7/2009 | Lange et al. | 528/25 |
| 7,563,857 B2 * | 7/2009 | Lange et al. | 528/28 |
| 7,585,494 B2 * | 9/2009 | Lange et al. | 424/70.122 |
| 7,863,397 B2 * | 1/2011 | Lange et al. | 528/28 |
| 7,897,716 B2 * | 3/2011 | Wagner et al. | 528/28 |
| 2004/0138400 A1 | 7/2004 | Lange et al. | |
| 2008/0242826 A1 | 10/2008 | Danner | |

FOREIGN PATENT DOCUMENTS

| | | |
|---|---|---|
| DE | 19540001 A1 | 5/1996 |
| DE | 10036694 A1 | 2/2002 |
| DE | 10036699 A1 | 2/2002 |
| DE | 102004012877 A1 | 7/2005 |
| WO | WO 02/10257 A1 * | 2/2002 |
| WO | WO2004/042136 * | 5/2004 |
| WO | 2004/056907 A2 | 7/2004 |
| WO | 2005/035628 A1 | 4/2005 |
| WO | WO 2005035628 * | 4/2005 |

OTHER PUBLICATIONS

Dega-Zafran et al. ARKIVOC 2007 (vi) 90-102.*
Espace patent abstract for DE 102004012877 published Jul. 21, 2005, one page.
Espace patent abstract for DE 19540001 published May 15, 1996, one page.
Espace patent abstract for DE 10036699 published Feb. 7, 2002, one page.
Espace patent abstract for DE 10036694 published Feb. 14, 2002, one page.
International Search Report for PCT/EP2006/064833 mailed Feb. 5, 2007, five pages.

* cited by examiner

*Primary Examiner* — Richard Schnizer
*Assistant Examiner* — Alma Pipic
(74) *Attorney, Agent, or Firm* — Rankin, Hill & Clark LLP

(57) ABSTRACT

The invention relates to linear copolymers of monomer units having both ammonium groups and polysiloxane groups. Amine oxide groups may be substituted for ammonium groups. The polymer backbone includes side chains having high densities of quaternary ammonium groups. The copolymers impart softening, antistatic, quick-drying and setting properties in the appropriate settings.

10 Claims, No Drawings

POLYAMMONIUM/POLYSILOXANE COPOLYMERS

This application is the national stage application under 35 U.S.C. 371 of PCT International Application No. PCT/EP2006/064833, filed Jul. 31, 2006 and published as WO2007/014930 on Feb. 8, 2007, and has designated the United States of America. The application claims priority of German Patent Application 10 2005 036 602.3, filed Aug. 1, 2005. The foregoing documents are incorporated by reference herein.

DESCRIPTION

The invention relates to polyammonium/polysiloxane copolymers, to processes for their preparation and to their use.

WO 2004/042136 discloses linear polyamino/polysiloxane copolymers and/or poly-ammonium/polysiloxane copolymers. The copolymers described there, especially with regard to their substantivity, i.e. the ability to adhere for as long as possible, especially in the presence of compositions with a high surfactant content, on the surface of a wide variety of different substrates, in order to exert the effects desired, especially their softening and possibly hydrophilizing effects, are still in need of improvement.

The inventors thus addressed the problem of providing novel polyammonium/poly-siloxane copolymers which possess new types of property profiles. Surprisingly, the inventors found that novel, especially linear, polyammonium/polysiloxane copolymers from whose polymer backbone side chains having quaternary ammonium groups project in high density possess new types of properties.

The present invention therefore provides polyammonium/polysiloxane copolymers containing repeat units of the formula (I):

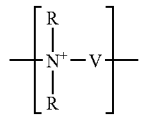
(I)

in which R are in each case independently organic groups which contain at least one group which is selected from quaternary ammonium groups and amine oxide groups,
V is selected from the $V^1$ and the $V^2$ group,
in which
$V^2$ is selected from divalent and trivalent, straight-chain, cyclic and branched, saturated, unsaturated and aromatic hydrocarbons having up to 1000 carbon atoms (not counting the carbon atoms of the polysiloxane radical $Z^2$ defined below), which may optionally contain one or more groups selected from
—O—,
—NR$^2$—,
—N$^+$R$^2_2$—,
  in which R$^2$ is hydrogen, a monovalent, straight-chain, cyclic or branched, saturated, unsaturated or aromatic hydrocarbon radical which has up to 100 carbon atoms and may contain one or more groups selected from —O—, —NH—, —C(O)— and —C(S)—, and which may optionally be substituted by one or more substituents selected from the group consisting of a hydroxyl group, an optionally substituted heterocyclic group preferably containing one or more nitrogen atoms, amino, alkylamino, dialkylamino, polyether radicals and polyetherester radicals, where, when a plurality of —NR$^2$— groups is present, they may be the same or different,
—C(O)—,
—C(S)—
and
the $V^2$ radical may optionally be substituted by one or more hydroxyl groups, and
the $V^2$ radical contains at least one —Z$^2$— group of the formula

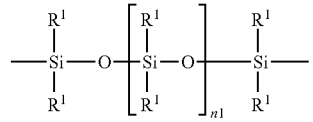

in which
R$^1$ may be the same or different and is selected from the group consisting of:
$C_1$ to $C_{22}$ alkyl, fluoro($C_1$-$C_{10}$)alkyl and $C_6$-$C_{10}$ aryl, and
$n_1$=20 to 1000,
$V^1$ is selected from divalent and trivalent, straight-chain, cyclic and branched, saturated, unsaturated and aromatic hydrocarbon radicals which have up to 1000 carbon atoms and may optionally contain one or more groups selected from
—O—,
—NR$^2$—,
—N$^+$R$^2_2$—.
  in which R$^2$ is as defined above, and where the R$^2$ groups in the $V^1$ and $V^2$ groups may be the same or different,
—C(O)—,
—C(S)— and
—Z$^1$—, in which —Z$^1$— is a group of the formula

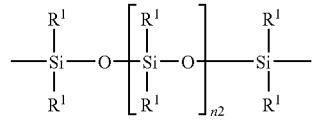

in which
R$^1$ is as defined above, where the R$^1$ groups in the $V^1$ and $V^2$ groups may the same or different, and
$n_2$=0 to 19,
and the $V^1$ radical may optionally be substituted by one or more hydroxyl groups,
in which the $V^1$ and $V^2$ groups in the polyammonium/polysiloxane copolymers may be the same or different, with the proviso that at least one $Z^1$ or $Z^2$ group is present, and
in which the positive charges resulting from the ammonium groups are neutralized by organic or inorganic acid anions. In a preferred embodiment, the R radicals are betaine radicals.

The inventive polyammonium/polysiloxane copolymers appropriately include at least two, preferably more than two, repeat units of the formula

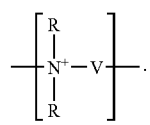
(I)

Two repeat units thus give rise to the following structure:

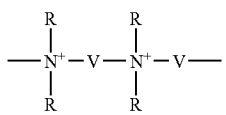

and three repeat units to the following structure:

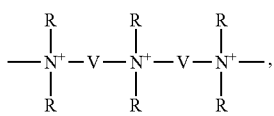

etc. The terminal nitrogen atoms are saturated by any monovalent organic radicals, and mention may be made especially of the radicals specified for $R^2$. The type of terminal groups arises generally from the type of starting materials or monomers used, or if appropriate from monovalent so-called stopper molecules which may be added to the reaction mixture.

Organic or inorganic acid anions are, for example, deprotonated organic and inorganic acids, such as deprotonated carboxylic acids, i.e. carboxylate anions such as acetate, propionate, octanoate, decanoate, dodecanoate, tetradecanoate, hexadecanoate, octadecanoate, oleate, citrate and benzoate, polyethercarboxylates, polyethersulfates, alkylsulfates, alkylsulfonates and arylsulfonates, or deprotonated mineral acids such as halides, especially chloride, sulfates, phosphates, nitrates, bromide, hydrogensulfate.

In a preferred embodiment of the inventive polyammonium/polysiloxane copolymers, the R radicals having quaternary ammonium groups are selected from groups of the formula (II):

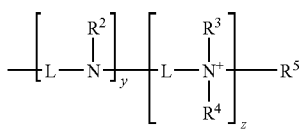

in which
L are in each case independently a divalent straight-chain, cyclic or branched, saturated, unsaturated or aromatic hydrocarbon radical which has up to 30 carbon atoms and may contain one or more groups selected from —O—, —NH—, —C(O)— and —C(S)—, and which may optionally be substituted by one or more substituents selected from the group consisting of a hydroxyl group, a carboxyl group, a carboxylate group, an optionally substituted heterocyclic group preferably containing one or more nitrogen atoms, amino, alkylamino, dialkylamino, ammonium group, polyether radicals and polyetherester radicals, $R^2$ is as defined above, preferably selected from: monovalent, straight-chain, cyclic and branched, saturated, unsaturated and aromatic hydrocarbon radicals which have up to 30 carbon atoms and may contain one or more groups selected from —O—, —NH—, —C(O)— and —C(S)—, and may optionally be substituted by one or more substituents selected from the group consisting of a hydroxyl group, a carboxyl group, a carboxylate group, an optionally substituted heterocyclic group preferably containing one or more nitrogen atoms, amino, alkylamino, dialkylamino, ammonium group, polyether radicals and polyetherester radicals, $R^3$, $R^4$ and $R^5$ are each independently selected from monovalent, straight-chain, cyclic and branched, saturated, unsaturated and aromatic hydrocarbon radicals which have up to 30 carbon atoms and may contain one or more groups selected from —O—, —NH—, —C(O)— and —C(S)—, and may optionally be substituted by one or more substituents selected from the group consisting of a hydroxyl group, a carboxyl group, a carboxylate group, an optionally substituted heterocyclic group preferably containing one or more nitrogen atoms, amino, alkylamino, dialkylamino, ammonium group, polyether radicals and polyetherester radicals, and $R^3$ or $R^4$ may be oxygen to form an amine oxide, and
z is 1 to 10 and y may be 0 to 10.

In the radical of the general formula (II), the radicals provided with the indices y and z may in principle be in any arrangement with respect to one another, for example randomly or blockwise. In each case, however, the radical of the general formula (II) has at least one quaternary ammonium group or an amine oxide group ($z \geq 1$), where the quaternary ammonium group is preferably a terminal group of the formula (III) generally described below.

In a further preferred embodiment of the inventive polyammonium/polysiloxane copolymers, the R radical is in each case a group of the formula (III):

in which L, $R^3$, $R^4$ and $R^5$ are each as defined above.

In a further preferred embodiment of the inventive polyammonium/polysiloxane copolymers, the R radical is in each case at least one amine oxide group of the formula (IV):

in which L, $R^3$ and $R^5$ are each as defined above.
L is preferably selected from $C_1$ to $C_{10}$-alkylene groups, which may be linear, branched or cyclic, for example methylene, ethylene, n-propylene, n-butylene, etc.

In a preferred embodiment of the invention, the polyammonium/polysiloxane copolymers have at least two repeat units V, more preferably at least two repeat units $V^2$.

In a preferred embodiment of the invention, $V^2$ is a group of the following formula

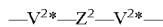

in which $Z^2$ is as defined above and $V^{2*}$ is a divalent straight-chain, cyclic or branched, saturated, unsaturated or aromatic hydrocarbon radical which has up to 40 carbon atoms and may optionally contain one or more groups selected from —O—, —$NR^2$—, —$N^+R^2{}_2$—, in which $R^2$ is as defined above, —C(O)— and —C(S)—, and the $V^{2*}$ radical may optionally be substituted by one or more hydroxyl groups.

In this connection, it is pointed out for clarification that, in the context of the present invention, the V, $V^1$, $V^2$ or $V^{2*}$ groups may likewise contain quaternary ammonium groups —$N^+R^2_2$—. However, the $R^2$ radical does not contain any quaternary ammonium groups. There is thus a clear distinction between the radical

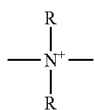

as present in formula (I) and the —$N^+R^2_2$— radical as may be present in V. An —$N^+R^2_2$— radical present in V may especially be a dimethylammonium group.

The $V^1$ group is preferably selected from divalent, straight-chain, cyclic and branched, saturated, unsaturated and aromatic hydrocarbon radicals which have up to 600 carbon atoms and may optionally contain one or more groups selected from —O—, —$NR^2$—, —$N^+R^2_2$—, in which $R^2$ is as defined above, —C(O)—, —C(S)—, and —$Z^1$—, in which $Z^1$ is a group of the formula

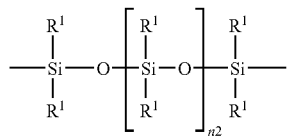

in which
$R^1$ is $C_1$ to $C_3$-alkyl, fluoro($C_3$-$C_6$)-alkyl or $C_6$-aryl, and $n_2$ is as defined above.

The present invention further relates to compounds of the formula (V):

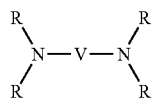

(V)

in which R and V are each as defined above, with the proviso that V contains $Z^1$ or $Z^2$, or an acid addition salt thereof. Acid addition salts means that at least one of the two nitrogen atoms visible in the general formula (V) is protonated by addition of a suitable acid to form the acid addition salt mentioned. Suitable acids are especially carboxylic acids such as acetic acid, and inorganic mineral acids such as hydrochloric acid, sulfuric acid, phosphoric acid, nitric acid, etc.

The compounds of the formula (V) are novel intermediates of the inventive polyammonium/polysiloxane copolymers. They accordingly have quaternary ammonium groups or amine oxide groups in the organic R radicals and can be converted by means of bifunctional quaternizing agents, as described below, to the inventive polyammonium/polysiloxane copolymers. In addition, it has been found in accordance with the invention that these compounds themselves, apparently owing to their high density of quaternary ammonium groups or amine oxide groups, can likewise be used for the inventive applications. The preparation of the compounds of the formula (V) or their acid addition salts succeeds, for example, by reaction of a polydimethylsiloxane having two terminal epoxy groups and a triamine with one internal secondary amino group and two external tertiary amino groups to form the compound of the formula (V') and subsequent quaternization of the resulting four tertiary amino groups as shown schematically below:

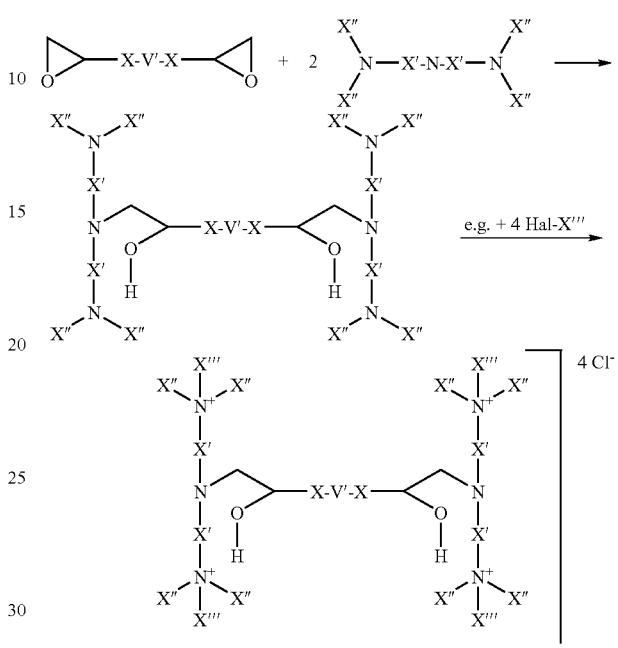

In this scheme, X and X' are each divalent organic radicals, V' is a divalent organic radical which has at least one $Z^1$ or $Z^2$ group, and X" and X''' are each monovalent organic radicals.

The invention further relates to the compounds of the formula (V'):

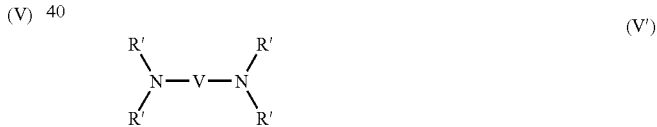

(V')

in which R' is in each case an organic group which contains at least one tertiary amino group, and V is as defined above, or an acid addition salt thereof. These compounds likewise constitute intermediates in the preparation of the inventive polyammonium/polysiloxane copolymers, and their acid addition salts in particular may also be used in the inventive applications.

In the compounds of the formula (V) and (V'), V is preferably $V^2$, i.e. preferably has the long-chain polysiloxane radical $Z^2$.

The invention further relates to a process for preparing the polyammonium/poly-siloxane copolymers, in which the compound of the formula (V) is reacted with at least one bifunctional (or else possibly higher-functionality) quaternizing agent. The bifunctional quaternizing agent is preferably selected from compounds which have two functional groups which are selected from the group consisting of epoxy groups and bishaloalkyl groups.

The starting point for the syntheses of the inventive substances is especially alpha,omega-SiH-functionalized siloxanes of the general structure

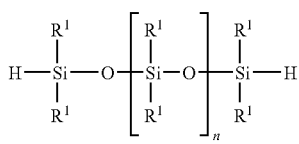

where $R^1$ is as defined above and n may be n1 or n2. When they are not commercially available, these siloxanes can be prepared by known processes, for example by equilibration (Silicone, Chemie und Technologie, Vulkan-Verlag, Essen 1989, p. 82-84).

Suitable starting materials for obtaining bifunctional alkylating agents are, for example, halogenated alkenes, especially allyl chloride and allyl bromide, unsaturated halocarboxylic esters, especially allyl chloroacetate, propargyl chloroacetate, allyl 3-chloropropionate and propargyl 3-chloropropionate, and epoxy-functional alkenes, for example vinylcyclohexene oxide and allyl glycidyl ether. The general performance of hydrosilylations with representatives of the substance groups mentioned is likewise known (B. Marciniec, Comprehensive Handbook on Hydrosilylation, Pergamon Press, Oxford 1992, p. 116-121, 127-130, 134-137, 151-155).

In a first step, the bifunctional alkylating agents are then reacted with polyamines, especially secondary-tertiary polyamines, the resulting products being alkylated on the secondary nitrogen atom, which results in tertiary nitrogen atoms. Suitable representatives of secondary-tertiary polyamines are, for example, N,N,N',N'-tetra-methyldiethylenetriamine, N,N,N',N'-tetramethylpropylenetriamine, N,N,N',N'-tetra-methyltriethylenetetramine, N,N,N',N'-tetramethyltripropylenetetramine, N,N,N',N'-tetramethyltetraethylenepentamine and N,N,N',N'-tetramethyltetrapropylenepentamine. This is generally followed by reaction with monofunctional alkylating agents such that at least two tertiary amino groups remain in the molecule, which can then be reacted with a bifunctional alkylating or quaternizing agent to give the inventive polyammonium/polysiloxane compounds.

Alternatively, the alkylation steps can also be effected in another sequence or by simultaneous addition of mono- and bifunctional alkylating agents with suitable stoichiometry.

Useful monofunctional quaternizing agents for the alpha, omega-polytertiary-amino-modified polysiloxanes include the known alkylating agents, such as alkyl halides, very especially $C_1$ to $C_{12}$-alkyl halides, or dialkyl sulfates, very especially dimethyl sulfate, or epoxides in the presence of stoichiometric amounts of acids HX, especially ethylene oxide, propylene oxide, hexene oxide, allyl glycidyl ether, isopropyl glycidyl ether and glycidyl methacrylate, or halocarboxylic esters.

The halocarboxylic esters are preferably synthesized from the corresponding alcohols or low molecular weight, oligomeric and polymeric alkylene oxides of the general composition

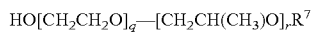

$$HO[CH_2CH_2O]_q\text{—}[CH_2CH(CH_3)O]_rR^7$$

where q, r and $R^7$ are each as defined above. Preferred alkoxylated representatives are the correspondingly monosubstituted derivatives of diethylene glycol, triethylene glycol, tetraethylene glycol, of the oligoethylene glycols with molar masses of 300 to 1000 g/mol, especially 400, 600 and 800, and also dipropylene glycol. These ethers and esters are prepared in a known manner by acid- or alkali-catalyzed addition of ethylene oxide and/or propylene oxide onto the corresponding alcohols (U.S. Pat. No. 5,625,024) or carboxylic acids (E. Sung, W. Umbach, H. Baumann, Fette Seifen Anstrichmittel 73, 88 [1971]).

The halocarboxylic esters are subsequently synthesized in a manner known per se by reaction with the $C_2$ to $C_4$-halocarboxylic acids, or their anhydrides or acid chlorides.

The selective synthesis of hydroxy-functional halocarboxylic esters ($R^4$=H) succeeds by addition of ethylene oxide and/or propylene oxide onto the corresponding halocarboxylic acids under acidic conditions.

The alpha,omega-poly-tertiary-amino-functionalized siloxane derivatives and the monofunctional quaternizing agents are reacted in a molar ratio which corresponds to the desired quaternization pattern, where the molar ratio Σ tertiary N:alkylating agent is ≧1:(1-1 mol of tertiary N), preferably Σ tertiary N:alkylating agent=1:(1-1 mol of tertiary N). In the presence of, for example, three tertiary amino functions on the siloxane chain end, consequently a maximum of two of these tertiary amino groups are alkylated with monofunctional agents.

The amount of alkylating agent has to be increased when secondary amino functions still present are additionally to be alkylated. This may be the case, for example, when the corresponding trialkylenetetramines or tetraalkylenepentamines are used, since only one secondary amino group in each case is required for their initial addition in alpha,omega position onto the reactive siloxane. The use of such higher polyamines allows the density of quaternized groups to be enhanced further. In these cases too, at least one tertiary amino group per chain end must remain for the final copolymer synthesis.

Suitable difunctional alkylating agents are, for example, dihaloalkanes such as 1,3-dichloropropane, 1,4-dichlorobutane and 1,6-dichlorohexane, dihaloalkenes and dihaloalkynes, e.g. 1,4-dichlorobut-2-yne, alpha,omega-halogen-substituted oligoalkylene oxides, the diesters of halocarboxylic acids with alkanediols, alkenediols or alkynediols, for example 1,4-but-2-ynol, oligoalkylene oxides, or polyols having two primary OH groups, e.g. sorbitol, and also the diepoxy derivatives of alkanes or the diepoxyether derivatives, especially glycidyl ether derivatives, of alkanediols and oligoalkylene oxides. The quaternizations with epoxides are effective in the presence of equivalent amounts of HX.

The introduction of hydrophilizing alkylene oxide blocks, which is preferred in one embodiment, succeeds preferably via the corresponding halocarboxylic esters or glycidyl ethers of the alkylene oxides. Preferred starting materials for their synthesis are low molecular weight, oligomeric and polymeric alkylene oxides of the general composition

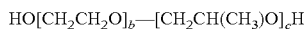

$$HO[CH_2CH_2O]_b\text{—}[CH_2CH(CH_3)O]_cH$$

where b and c are each as defined above. Preferred representatives with regard to the alkylene oxide block are diethylene glycol, triethylene glycol, tetraethylene glycol, the oligoethylene glycols with molar masses of 300 to 1000 g/mol, especially 400, 600 and 800, and also dipropylene glycol.

Alpha,omega-glycidyl ethers are obtainable by a reaction of epichlorohydrin with the corresponding alkylene oxides in the presence of alkali metal hydroxides.

The alkylene oxides are esterified in a manner known per se by reaction with the $C_2$-$C_4$-halocarboxylic acids, or their anhydrides or acid chlorides.

Preference is given to using the acid chlorides of chloroacetic acid and 3-chloropropionic acid, and to performing the reaction in the absence of solvents.

In a specific embodiment, the reactive difunctional intermediates already illustrated in detail above, such as alpha, omega-haloalkyl-substituted siloxanes, alpha,omega-halocarboxylic ester-substituted siloxanes, or alpha,omega-epoxide-substituted siloxanes, serve as comonomers. This procedure opens up the possibility of further increasing the proportion of very flexible, hydrophobic structural elements if required.

The inorganic or organic anions needed to balance the charge are preferably represented by physiologically compatible inorganic radicals such as chloride, bromide, hydrogensulfate, sulfate, or organic radicals such as acetate, propionate, octanoate, decanoate, dodecanoate, tetradecanoate, hexadecanoate, octadecanoate, oleate, citrate and benzoate, polyethercarboxylates, polyethersulfates, alkylsulfates, alkylsulfonates and arylsulfonates.

The amine oxide derivatives are synthesized in an analogous manner. To this end, the alpha,omega-poly-tertiary-amino-modified polysiloxanes are reacted with inorganic or organic peroxides. The performance of amine oxide syntheses is common knowledge (Houben/Weyl, Methoden der Organischen Chemie [Methods of organic chemistry], Volume XI/2, p. 191-194 and Volume E16a, p. 408-412). Preferred peroxides are, for example, hydrogen peroxide, peracetic acid and perbenzoate acid. It is possible to release the peroxides "in situ" from corresponding salts, for example percarbonates and perborates.

It is within the scope of the invention to react a plurality of siloxane components of different chain length and/or different secondary-tertiary polyamines while retaining the desired overall stoichiometry. This gives rise, for example, to the possibility of establishing a desired siloxane chain length by using a single siloxane component or else by controlled mixing of a plurality of siloxane components. Analogously thereto, it is possible to establish an advantageous average density of quaternized groups in the alpha,omega position on the siloxane.

The quaternization reactions and amine oxide syntheses are preferably conducted in water and/or polar organic solvents. Suitable examples are alcohols, especially methanol, ethanol, i-propanol, and n-butanol, glycols such as ethylene glycol, diethylene glycol, triethylene glycol, the methyl, ethyl and butyl ethers of the glycols mentioned, 1,2-propylene glycol and 1,3-propylene glycol, ketones such as acetone and methyl ethyl ketone, esters such as ethyl acetate, butyl acetate and 2-ethylhexyl acetate, ethers such as tetrahydrofuran, and nitro compounds such as nitromethane. The selection of the solvent is guided essentially by the solubility of the reactants and the desired reaction temperature.

The reactions are conducted in the range from 20° C. to 130° C., preferably from 40° C. to 100° C.

The invention further relates to the use of the inventive polyammonium-polysiloxane copolymers and of the compounds of the formulae (V) and (V') or their acid addition salts in cosmetic formulations for skincare and haircare.

The invention further relates to the use of the inventive polyammonium-polysiloxane copolymers and of the compounds of the formulae (V) and (V') or their acid addition salts in polishes for the treatment and finishing of hard surfaces, in formulations for drying automobiles and other hard surfaces after machine washing.

The invention further relates to the use of the inventive polyammonium-polysiloxane copolymers and of the compounds of the formulae (V) and (V') or their acid addition salts for finishing or treatment of textiles, textile fibers, paper and wood.

The invention further relates to the use of the inventive polyammonium-polysiloxane copolymers and of the compounds of the formulae (V) and (V') or their acid addition salts as an antistat and/or antibacterial agent.

The invention further relates to the use of the inventive polyammonium-polysiloxane copolymers and of the compounds of the formulae (V) and (V') or their acid addition salts as separate softeners after the washing of textiles with formulations based on anionic and/or nonionic detergents and as softeners in formulations based on anionic and/or nonionic surfactants for textile laundry.

The invention further relates to the use of the inventive polyammonium-polysiloxane copolymers and of the compounds of the formulae (V) and (V') or their acid addition salts as a component for improving hair shine in shampoos which are based on anionic, nonionic, cationic or betaine-type surfactants, in transparent or turbid "leave-on" or "rinse-off" hair-setting compositions, hair-setting foams, hair-setting gels and hair-setting sprays.

The invention further relates to the use of the inventive polyammonium-polysiloxane copolymers and of the compounds of the formulae (V) and (V') or their acid addition salts as a component as an assistant in hair dyeing or for retarding bleeding/washing of dyes out of dyed hair in shampoos which are based on anionic, nonionic, cationic or betaine-type surfactants, in transparent or turbid "leave-on" or "rinse-off" hair-setting compositions, hair-setting foams, hair-setting gels and hair-setting sprays.

The invention further relates to the use of the inventive polyammonium-polysiloxane copolymers and of the compounds of the formulae (V) and (V') or their acid addition salts as a component for improving hair volume in shampoos which are based on anionic, nonionic, cationic or betaine-type surfactants, in transparent or turbid "leave-on" or "rinse-off" hair-setting compositions, hair-setting foams, hair-setting gels and hair-setting sprays.

The invention further relates to the use of the inventive polyammonium-polysiloxane copolymers and of the compounds of the formulae (V) and (V') or their acid addition salts as a component for reducing combing forces in shampoos which are based on anionic, nonionic, cationic or betaine-type surfactants, in transparent or turbid "leave-on" or "rinse-off" hair-setting compositions, hair-setting foams, hair-setting gels and hair-setting sprays.

The invention further relates to the use of the inventive polyammonium-polysiloxane copolymers and of the compounds of the formulae (V) and (V') or their acid addition salts as a component for improving permanence of hair-setting compositions in shampoos which are based on anionic, nonionic, cationic or betaine-type surfactants, in transparent or turbid "leave-on" or "rinse-off" hair-setting compositions, hair-setting foams, hair-setting gels and hair-setting sprays.

The invention further relates to compositions comprising the inventive polyammonium/polysiloxane copolymers and/or the compounds of the formulae (V) and (V') or their acid addition salts together with at least one further ingredient customary for such a composition, such as a washing composition, polishing composition or a cosmetic composition.

EXAMPLES

Example 1

116.3 g (0.0184 mol of epoxy groups) of an epoxy siloxane of average composition

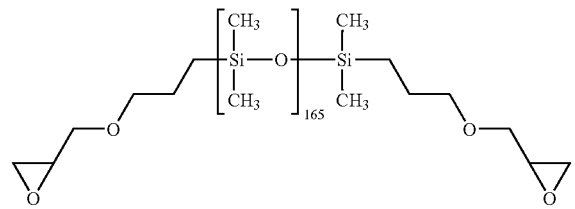

and 3.44 g (0.0184 mol) of N,N,N',N'-tetramethyldipropylenetriamine are dissolved in 120 g of i-propanol and heated to reflux temperature for 8 hours. 7.2 g (0.0368 mol) of 39% peracetic acid are added dropwise to the hexa-tertiary amino derivative formed within 10 minutes, and the reaction is continued for 6 hours. In the course of the reaction, the solution takes on a slightly reddish color. A test with potassium iodide and starch indicates that no further free peroxide is present on completion of the reaction. After the solvent has been removed under reduced pressure, 117.2 g of a viscous material of the following structure are obtained:

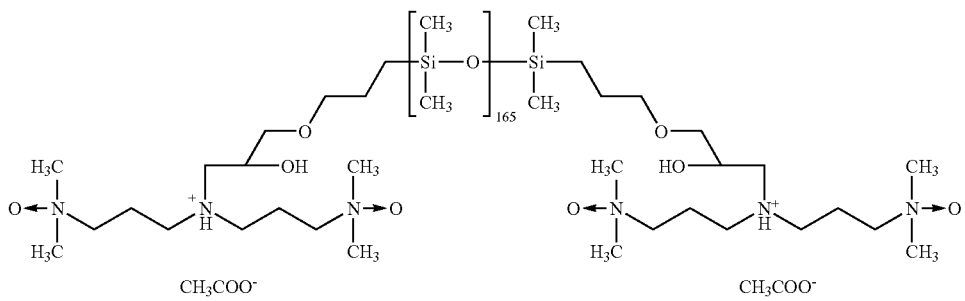

¹H NMR for Hexa-tertiary Amino Derivative Formed as an Intermediate

| Substructure | shift (ppm) |
|---|---|
| —SiCH₂— | 0.45-0.5 (2H) |
| —CH(OH)CH₂N[CH₂CH₂CH₂N(CH₃)₂]₂ | 2.3-2.5 (6H) |
| —CH(OH)CH₂N[CH₂CH₂CH₂N(CH₃)₂]₂ | 2.15-2.22 (4H) |
| —CH(OH)CH₂N[CH₂CH₂CH₂N(CH₃)₂]₂ | 2.1 (12H) |

¹H NMR for Amine Oxide

| Substructure | shift (ppm) |
|---|---|
| —SiCH₂— | 0.4-0.5 (2H) |
| —CH(OH)CH₂N[CH₂CH₂CH₂NO(CH₃)₂]₂ | 3.17-3.27 (12H) |

Example 2

2a) 41.5 g (0.223 mol) of dedecanol are initially charged at room temperature under nitrogen. With vigorous stirring, 37.7 g (0.334 mol) of chloroacetyl chloride are added dropwise within 10 minutes. During the dropwise addition, the temperature rises to 45° C. and intense HCl evolution sets in. After the dropwise addition has ended, the mixture is heated to 100° C. for 2 hours. Finally, all constituents which boil up to 100° C./20 hPa are distilled off. 57.8 g of a slightly yellow-colored, low-viscosity chloroacetic ester of the formula ClCH₂C(O)O(CH₂)₁₁CH₃ are obtained.

The purity of the ester determined by gas chromatography is greater than 99%.

2b) 65.4 g (0.0104 mol of epoxy groups) of a epoxy siloxane of average composition

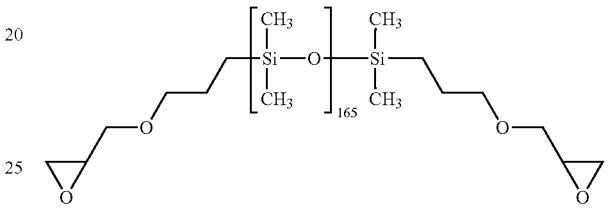

and 1.9 g (0.0104 mol) of N,N,N',N'-tetramethyldipropylenetriamine are dissolved in 72.7 g of i-propanol, and the mixture is heated to reflux temperature for 8 hours. Subsequently, 5.4 g (0.0207 mol) of the chloroacetic ester according to Example 2a) are added, and the reaction is continued for 7 hours. After the solvent has been removed, 69.8 g of yellowish, viscous material of the structure

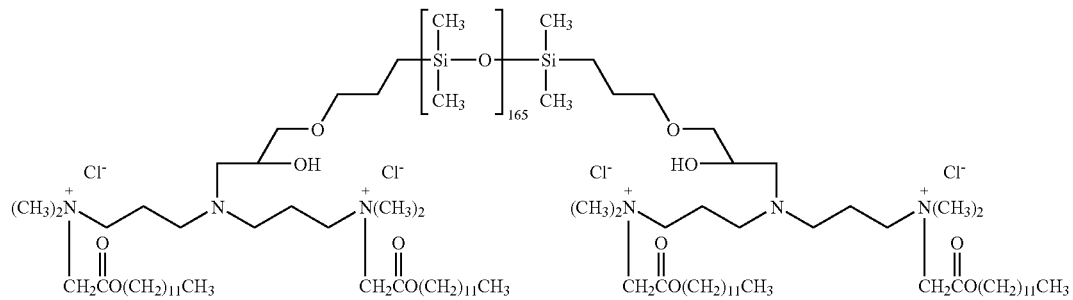

are obtained.

By gas chromatography, a quantitative conversion of the ester was found.

¹H NMR for Quaternary Material

| Substructure | shift (ppm) |
|---|---|
| —SiCH₂— | 0.4-0.5 (2H) |
| —CH(OH)CH₂N[CH₂CH₂CH₂N⁺(CH₂—)(CH₃)₂]₂ | 3.35-3.51 (12H) |

Example 3

To demonstrate the softening properties, bleached cotton strips which had not been modified further on the surface were subjected to a wash process in the presence of Ariel Future®, bentonite-containing Dash 2 in 1®, and the poly-quaternary siloxane described in Example 2b. The following boundary conditions were maintained.

removed, 39 g of a yellow-beige viscous product with structural units

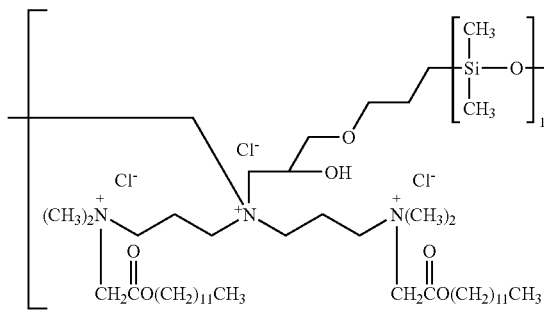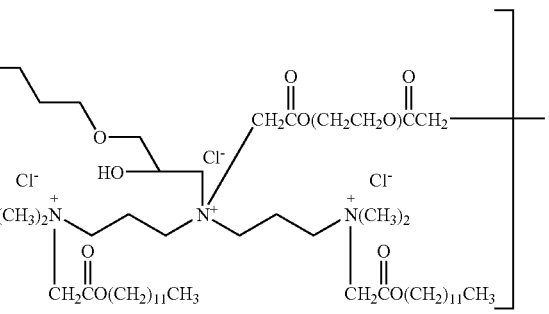

are obtained.

$^1$H NMR

| Substructure | shift (ppm) |
|---|---|
| —N$^+$CH$_2$—C(O)O— | 4.07 |

|  | Strip 1 | Strip 2 | Strip 3 |
|---|---|---|---|
| Strip weight (g) | 13.07 | 12.70 | 13.30 |
| Amount of water (ml) | 653 | 645 | 666 |
| Detergent (g) | 0.65 Ariel Future ® | 0.64 Dash 2 in 1 ® | 0.67 Ariel Future ® |
| Ester quat Ex. 2b (g) | 0.2 | — | — |
| Ø mark | 1.2 | 1.9 | 2.9 |

The water is heated to 60° C., and the detergents and, in the case of cotton strip 1, additionally the poly-quaternary siloxane according to Example 2b are dissolved. Subsequently, the cotton strips are washed in the solutions for 30 minutes. Subsequently, the strips are rinsed in 5 600 ml of water and then dried at 120° C. for 30 minutes.

16 test subjects rated the three cotton strips for the softness of the hand, the mark 1 having been assigned to the softest strip and the mark 3 to the strip found to be the hardest.

As a result of the assessment, cotton strip 1 received the average mark of 1.2. The bentonite-treated cotton strip 2 was rated with an average of 1.9, and strip 3 at 2.9.

Example 4

4a) 238 g (2.24 mol) of diethylene glycol are initially charged at room temperature under nitrogen. With vigorous stirring, 558 g (4.93 mol) of chloroacetyl chloride are added dropwise within one hour. During the dropwise addition, the temperature rises to 82° C., and intense HCl evolution sets in. After the dropwise addition has ended, the mixture is heated to 130° C. for 30 minutes. Finally, all constituents which boil up to 130° C./20 hPa are distilled off. 566 g of a pale yellow oil of composition ClCH$_2$C(O)OCH$_2$CH$_2$OCH$_2$CH$_2$OC(O)CH$_2$Cl are obtained.

The purity of the ester, determined by gas chromatography, is 99.2%.

$^{13}$C NMR:

| Substructure | Shift (ppm) |
|---|---|
| ClCH$_2$— | 40.7 |
| ClCH$_2$—C(O)— | 167.1 |
| ClCH$_2$—CH$_2$—C(O)—OCH$_2$— | 65.2 |
| ClCH$_2$—CH$_2$—C(O)—OCH$_2$CH$_2$— | 68.6 |

42.4 g (0.00151 mol) of the quaternarized siloxane according to Example 2b and 1.59 g (0.00151 mol) of the diesters according to Example 4a) are dissolved in 45 g of i-propanol, and the mixture is heated to reflux temperature for 8 hours. The clear mixture becomes cloudy in the course of cooling after the reaction has ended. After the solvent has been

Example 5

To demonstrate the softening properties, bleached cotton strips which had not been modified further on the surface were subjected to a wash process in the process of Ariel Future®, bentonite-containing Dash 2 in 1®, and the poly-quaternary siloxane described in Example 4. The following boundary conditions were maintained.

|  | Strip 1 | Strip 2 | Strip 3 |
|---|---|---|---|
| Strip weight (g) | 13.11 | 13.25 | 13.31 |
| Amount of water (ml) | 654 | 664 | 667 |
| Detergent (g) | 0.65 Ariel Future ® | 0.66 Dash 2 in 1 ® | 0.67 Ariel Future ® |
| Ester quat Ex. 2b (g) | 0.2 | — | — |
| Ø mark | 1.4 | 1.8 | 2.8 |

The water is heated to 60° C., and the detergents and, in the case of cotton strip 1, additionally the poly-quaternary siloxane according to Example 4 are dissolved. Subsequently, the cotton strips are washed in the solutions for 30 minutes. Subsequently, the strips are rinsed in 5 600 ml of water and then dried at 120° C. for 30 minutes.

16 test subjects rated the three cotton strips for the softness of the hand, the mark 1 having been assigned to the softest strip and the mark 3 to the strip found to be the hardest.

As a result of the assessment, cotton strip 1 received the average mark of 1.4. The bentonite-treated cotton strip 2 was rated with an average of 1.8, and strip 3 at 2.8.

Example 6a

| Anionic shampoo (numerical values are % by weight) | |
|---|---|
| Inventive component | 0.5 to 5 |
| Ammonium lauryl sulfate* | 10.00-30.00 |
| Ammonium laureth sulfate* | 5.00-20.00 |

Anionic shampoo
(numerical values are % by weight)

| | |
|---|---|
| Cocamidopropyl betaine* | 0.00-15.00 |
| Lauramide DEA* | 0.00-5.00 |
| Cocamide Mea* | 0.00-5.00 |
| Dimethicone copolyol* | 0.00-5.00 |
| Cyclopentasiloxane* | 0.00-5.00 |
| Quaternary silicone* | 0.50-5.00 |
| Polyquaternium-10* | 0.00-2.00 |
| Preservative* | 0.00-0.50 |
| Fragrance* | 0.00-5.00 |
| Deionized water* | q.s. 100% |
| Sodium chloride* | q.s. |

*INCI name

This formulation constitutes a framework recipe. Formulations of this category comprise the following components, without being restricted to them:

alkyl sulfates, alkyl ether sulfates, sodium lauryl sulfate, sodium laureth sulfate, ammonium lauryl sulfate, ammonium laureth sulfate, TEA lauryl sulfate, TEA laureth sulfate, alkylbenzenesulfonates, alpha-olefinsulfonates, paraffin-sulfonates, sulfosuccinates, N-acyltaurides, sulfated glycerides, sulfated alkanolamides, carboxylate salts, N-acylamino acid salts, silicones.

Example 6b

Nonionic shampoo
(numerical values are % by weight)

| | |
|---|---|
| Inventive component | 0.5 to 5 |
| Lauramide DEA* | 10.00-30.00 |
| Lauramide oxide* | 5.00-20.00 |
| Cocamide Mea* | 0.00-5.00 |
| Dimethicone copolyol* | 0.00-5.00 |
| Quaternary silicone* | 0.50-5.00 |
| Preservative* | 0.00-0.50 |
| Fragrance* | 0.00-5.00 |
| Deionized water* | q.s. 100% |
| Sodium chloride* | q.s. |

*INCI name

This formulation constitutes a framework recipe. Formulations of this category comprise the following components, without being restricted thereto:

monoalkanolamides, monoethanolamides, monoisopropanolamides, polyhydroxy derivatives, sucrose monolaurate, polyglycerol ethers, amine oxides, polyethoxylated derivatives, sorbitan derivatives, silicones.

Example 6c

Amphoteric shampoo
(numerical values are % by weight)

| | |
|---|---|
| Inventive component | 0.5 to 5 |
| PEG-80 sorbitan laurate* | 10.00-30.00 |
| Lauroamphoglycinate* | 0.00-10.00 |
| Cocamidopropyl hydroxysultaine* | 0.00-15.00 |
| PEG-150 distearate* | 0.00-5.00 |
| Laureth-13 carboxylate* | 0.00-5.00 |
| Quaternary silicone* | 0.50-5.00 |
| Preservative* | 0.00-0.50 |
| Fragrance* | 0.00-5.00 |
| Deionized water* | q.s. 100% |
| Sodium chloride* | q.s. |

*INCI name

This formulation is a framework recipe. Formulations of this category comprise the following components, without being restricted thereto:

N-alkyl-α-iminodipropionate, N-alkyl-α-iminopropionate, amino acids, amino acid derivatives, amidobetaines, imidazolinium derivatives, sulfobetaines, sultanines, betaines, silicones.

Example 6d

Cationic shampoo
(numerical values are % by weight)

| | |
|---|---|
| Inventive component | 0.5 to 5 |
| Laureth-13 carboxylate* | 10.00-30.00 |
| Isopropyl myristate* | 5.00-20.00 |
| Cocamidopropyl betaine* | 0.00-15.00 |
| Lauramide DEA* | 0.00-5.00 |
| Cocamide Mea* | 0.00-5.00 |
| Quaternary silicone* | 0.50-5.00 |
| Quaternary silicone* | 0.50-5.00 |
| Preservative* | 0.00-0.50 |
| Fragrance* | 0.00-5.00 |
| Deionized water* | q.s. 100% |
| Sodium chloride* | q.s. |

*INCI name

This formulation is a framework recipe. Formulations of this category comprise the following components, without being restricted thereto:

bis-quaternary ammonium compounds, bis(trialkyammonioacetyl)diamines, amidoamines, ammonioalkyl esters, silicones.

Example 6e

Hair-setting composition
(numerical values are % by weight)

| | |
|---|---|
| Inventive component | 0.5 to 5 |
| Ceteareth-20* | 0.10-10.00 |
| Steareth-20* | 0.10-10.00 |
| Stearyl alcohol* | 0.10-10.00 |
| Stearamidopropyl dimethylamine* | 0.00-10.00 |
| Dicetyldimonium chloride* | 0.00-10.00 |
| Quaternary silicone* | 0.50-5.00 |
| Cyclopentasiloxane* | 0.00-5.00 |
| Dimethicone* | 0.00-5.00 |
| Preservative* | 0.00-5.00 |
| Fragrance* | 0.00-0.50 |
| Deionized water* | q.s. 100% |

*INCI name

This formulation is a framework recipe. Formulations of this category comprise the following components, without being restricted thereto:

fatty acids, fatty acid esters, ethoxylated fatty acids, ethoxylate fatty acid esters, fatty alcohols, ethoxylated fatty alcohols, glycol, glycol esters, glycerol, glycerol esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickeners, silicones.

Example 6f

"Clear rinse-off" hair-setting compositions
(numerical values are % by weight)

| | |
|---|---|
| Inventive component | 0.5 to 5 |
| Glycerin* | 0.10-10.00 |
| Cetrimonium chloride* | 0.00-10.00 |
| Quaternary silicone* | 0.50-5.00 |
| Hydroxyethylcellulose* | 0.00-5.00 |
| Preservative* | 0.00-0.50 |
| Fragrance* | 0.00-5.00 |
| Deionized water* | q.s. 100% |

*INCI name

This formulation is a framework recipe. Formulations of this category comprise the following components, without being restricted thereto:

fatty acids, fatty acid esters, ethoxylated fatty acids, ethoxylated fatty acid esters, fatty alcohols, ethoxylated fatty alcohols, glycol, glycol esters, glycerol, glycerol esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickeners, silicones.

Example 6 g

Setting foam for hair
(numerical values are % by weight)

| | |
|---|---|
| Inventive component | 0.5 to 5 |
| Quaternary silicone* | 0.50-5.00 |
| Nonoxynol-15* | 0.00-2.00 |
| Nonoxynol-20* | 0.00-2.00 |
| Fragrance* | 0.00-5.00 |
| Propellant* | 0.00-20.00 |
| Preservative* | 0.00-0.50 |
| Fragrance* | 0.00-5.00 |
| Deionized water* | q.s. 100% |

*INCI name

This formulation is a framework recipe. Formulations of this category comprise the following components, without being restricted thereto:

fatty acids, fatty acid esters, ethoxylated fatty acids, ethoxylated fatty acid esters, fatty alcohols, ethoxylated fatty alcohols, glycol, glycol esters, glycerol, glycerol esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickeners, silicones, solvents, ethanol, isopropanol, isoparaffinic solvents, butane, propane, isobutane, CFCs, fluorinated propellants, dimethyl ether, compressed gases.

Example 6 h

Pump spray (setting composition) for hair
(numerical values are % by weight)

| | |
|---|---|
| Inventive component | 0.5 to 5 |
| Quaternary silicone* | 0.50-5.00 |
| Cyclomethicone* | 0.00-80.00 |
| Ethanol* | 0.00-80.00 |
| Preservative* | 0.00-0.50 |
| Fragrance* | 0.00-5.00 |
| Deionized water* | q.s. 100% |

*INCI name

This formulation is a framework recipe. Formulations of this category comprise the following components, without being restricted thereto:

fatty acids, fatty acid esters, ethoxylated fatty acids, ethoxylated fatty acid esters, fatty alcohols, ethoxylated fatty alcohols, glycol, glycol esters, glycerol, glycerol esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickeners, silicones, solvents, ethanol, isopropanol, isoparaffinic solvents, butane, propane, isobutane, CFCs, fluorinated propellants, dimethyl ether, compressed gases.

Example 6i

Setting spray for hair
(numerical values are % by weight)

| | |
|---|---|
| Inventive component | 0.5 to 5 |
| Quaternary silicone* | 0.50-5.00 |
| Cyclomethicone* | 0.00-80.00 |
| Ethanol* | 0.00-50.00 |
| Propellant* | 0.00-50.00 |
| Preservative* | 0.00-0.50 |
| Fragrance* | 0.00-5.00 |
| Deionized water* | q.s. 100% |

*INCI name

This formulation is a framework recipe. Formulations of this category comprise the following components, without being restricted thereto:

fatty acids, fatty acid esters, ethoxylated fatty acids, ethoxylated fatty acid esters, fatty alcohols, ethoxylated fatty alcohols, glycol, glycol esters, glycerol, glycerol esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, thickeners, silicones, solvents, ethanol, isopropanol, isoparaffinic solvents, butane, propane, isobutane, CFCs, fluorinated propellants, dimethyl ether, compressed gases.

Example 6j

| Setting gel for hair (numerical values are % by weight) | |
| --- | --- |
| Inventive component | 0.5 to 5 |
| Quaternary silicone* | 0.50-5.00 |
| Hydroxyethylcellulose* | 0.00-2.00 |
| Fragrance* | 0.00-5.00 |
| Preservative* | 0.00-0.50 |
| Citric acid* | 0.00-2.00 |
| Deionized water* | q.s. 100% |

*INCI name

This formulation is a framework recipe. Formulations of this category comprise the following components, without being restricted thereto:
thickeners, cellulose derivatives, acrylic acid derivatives, fixative polymers, conditioner chemicals, glycol, glycol esters, glycerol, glycerol esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, silicones, solvents, ethanol, isopropanol, isoparaffinic solvents.

Example 6k

| Styling gel for hair (numerical values are % by weight) | |
| --- | --- |
| Inventive component | 0.5 to 5 |
| Quaternary silicone* | 0.50-5.00 |
| Fixative* | 0.10-10.00 |
| Hydroxyethylcellulose* | 0.00-2.00 |
| Fragrance* | 0.00-5.00 |
| Fragrance* | 0.00-5.00 |
| Citric acid* | 0.00-2.00 |
| Deionized water* | q.s. 100% |

*INCI name

This formulation is a framework recipe. Formulations of this category comprise the following components, without being restricted thereto:
fixative polymers, varnishes, thickeners, cellulose derivatives, acrylic acid derivatives, conditioner chemicals, glycol, glycol esters, glycerol, glycerol esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, silicones, solvents, ethanol, isopropanol, isoparaffinic solvents.

Example 6l

| Styling spray for hair (numerical values are % by weight) | |
| --- | --- |
| Inventive component | 0.5 to 5 |
| Quaternary silicone* | 0.50-5.00 |
| Cyclomethicone* | 0.00-80.00 |
| Fixative* | 0.10-10.00 |
| Ethanol* | 0.00-50.00 |
| Propellant* | 0.00-50.00 |
| Preservative* | 0.00-0.50 |
| Fragrance* | 0.00-5.00 |
| Deionized water* | q.s. 100% |

*INCI name

This formulation is a framework recipe. Formulations of this category comprise the following components, without being restricted thereto:
fixative polymers, varnishes, thickeners, cellulose derivatives, acrylic acid derivatives, conditioner chemicals, glycol, glycol esters, glycerol, glycerol esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, silicones, solvents, ethanol, isopropanol, isoparaffinic solvents, butane, propane, isobutane, CFCs, fluorinated propellants, dimethyl ether, compressed gases.

Example 6m

| Pump spray (styling) for hair (numerical values are % by weight) | |
| --- | --- |
| Inventive component | 0.5 to 5 |
| Quaternary silicone* | 0.50-5.00 |
| Fixative* | 0.10-10.00 |
| Cyclomethicone* | 0.00-80.00 |
| Ethanol* | 0.00-50.00 |
| Preservative* | 0.00-0.50 |
| Fragrance* | 0.00-5.00 |
| Deionized water* | q.s. 100% |

*INCI name

This formulation is a framework recipe. Formulations of this category comprise the following components, without being restricted thereto:
vinyl derivatives, fixative polymers, varnishes, thickeners, fatty acids, fatty acid esters, ethoxylated fatty acids, ethoxylated fatty acid esters, fatty alcohols, ethoxylated fatty alcohols, cellulose derivatives, acrylic acid derivatives, conditioner chemicals, glycol, glycol esters, glycerol, glycerol esters, lanolin, lanolin derivatives, mineral oil, petrolatum, lecithin, lecithin derivatives, waxes, wax derivatives, cationic polymers, proteins, protein derivatives, amino acids, amino acid derivatives, humectants, silicones, solvents, ethanol, isopropanol, isoparaffinic solvents, butane, propane, isobutane, CFCs, fluorinated propellants, dimethyl ether, compressed gases.

A positive influence on the following effects can be expected from the inventive siloxane derivatives when used in the hair cosmetics sector:
1 Stabilization
2 Shine
3 Fixing (hold)
4 Body
5 Volume
6 Moisture regulation
7 Color retention
8 Protection from environmental influences (UV, salt water, etc.)
9 Reshapeability
10 Antistatic properties
11 Dyeability

The invention claimed is:

1. A polyammonium/polysiloxane copolymer; comprising repeat units of the formula (I):

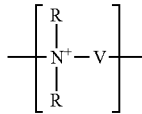
(I)

wherein groups R are independently organic groups which contain at least one selected from the group consisting of quaternary ammonium groups and amine oxide groups, wherein V is selected from a plurality of groups $V^1$ and a plurality of groups $V^2$, wherein the plurality of groups $V^1$ may be the same or different, and the plurality of groups $V^2$ may be the same or different, in which $V^2$ is selected from divalent and trivalent, straight-chain, cyclic and branched, saturated, unsaturated and aromatic hydrocarbons including at least one $Z^2$ group of the formula

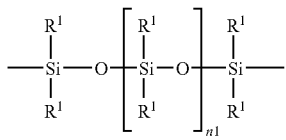

wherein groups $R^1$ may be the same or different and are selected from the group consisting of $C_1$-$C_{22}$ alkyl, fluoro ($C_1$-$C_{10}$) alkyl, and $C_6$-$C_{10}$ aryl, and wherein $n_1$=20 to 1000, wherein $V^2$ includes up to 1000 carbon atoms exclusive of the $Z^2$ group, and wherein $V^2$ may optionally contain one or more groups selected from
—OH,
—O—,
—$NR^2$—,
—$N^+R^2_2$—, in which $R^2$ is hydrogen, a monovalent, straight-chain, cyclic or branched, saturated, unsaturated or aromatic hydrocarbon radical which has up to 100 carbon atoms and may contain one or more groups selected from —O—, —NH—, —C(O)— and —C(S)—, and which may optionally be substituted by one or more substituents selected from the group consisting of a hydroxyl group, an optionally substituted heterocyclic group containing one or more nitrogen atoms, amino, alkylamino, dialkylamino, polyether radicals and polyetherester radicals, where, when a plurality of —$NR^2$-groups is present, they may be the same or different,
—C(O)—,
—C(S)—
and wherein $V^1$ is selected from divalent and trivalent, straight-chain, cyclic and branched, saturated, unsaturated and aromatic hydrocarbon radicals which have up to 1000 carbon atoms and may optionally contain one or more groups selected from
—OH,
—O—,
—$NR^2$—,
—$N^+R^2_2$—, in which $R^2$ is as defined above, and where the $R^2$ groups in the $V^1$ and $V^2$ groups may be the same or different,
—C(O)—,
—C(S)— and
—$Z^1$—, in which —$Z^1$— is a group of the formula

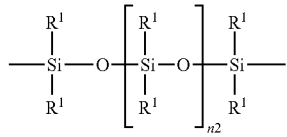

in which
$R^1$ is as defined above, where the $R^1$ groups in the $V^1$ and $V^2$ groups may the same or different, $n_2$=0 to 19, wherein at least one $Z^1$ or $Z^2$ group is present, and
wherein acid anions neutralize the ammonium groups.

2. The polyammonium/polysiloxane copolymer of claim 1, wherein each R is at least one group of the formula (II):

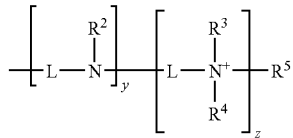
(II)

in which
each group L is independently a divalent straight-chain, cyclic or branched, saturated, unsaturated or aromatic hydrocarbon radical which has up to 30 carbon atoms and may contain one or more groups selected from —O—, —NH—, —C(O)— and —C(S)—, and may optionally be substituted by one or more substituents selected from the group consisting of a hydroxyl group, a carboxyl group, a carboxylate group, and an optionally substituted heterocyclic group optionally containing one or more selected from the group consisting of nitrogen atoms, amino, alkylamino, dialkylamino, ammonium group, polyether radicals and polyetherester radicals, $R^2$ is as defined in claim 1,
$R^3$, $R^4$ and $R^5$ are each independently selected from monovalent, straight-chain, cyclic and branched, saturated, unsaturated and aromatic hydrocarbon radicals which have up to 30 carbon atoms and may contain one or more groups selected from —O—, —NH—, —C(O)— and —C(S)—, and may optionally be substituted by one or more substituents selected from the group consisting of a hydroxyl group, a carboxyl group, a carboxylate group, and an optionally substituted heterocyclic group containing one or more nitrogen atoms, amino, alkylamino, dialkylamino, ammonium group, polyether radicals and polyetherester radicals, and
$R^3$ or $R^4$ may be oxygen to form an amine oxide, and
z is 1 to 10 and y is from 0 to 10.

3. The polyammonium/polysiloxane copolymer of claim 1, wherein
R has the formula (III):

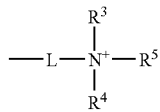
(III)

in which L, is in each case independently a divalent straight-chain, cyclic or branched, saturated, unsaturated or aromatic hydrocarbon radical which has up to 30 carbon atoms and may contain one or more groups selected from —O—, —NH—, —C(O)— and —C(S)—, and which may optionally be substituted by one or more substituents selected from the group consisting of a hydroxyl group, a carboxyl group, a carboxylate group, an optionally substituted heterocyclic group optionally containing one or more nitrogen atoms, amino, alkylamino, dialkylamino, ammonium group, polyether radicals and polyetherester radicals, $R^3$, $R^4$ and $R^5$ are each independently selected from monovalent, straight-chain, cyclic and branched, saturated, unsaturated and aromatic hydrocarbon radicals which have up to 30 carbon atoms and may contain one or more groups selected from —O—, —NH—, —C(O)— and —C(S)—, and may optionally be substituted by one or more substituents selected from the group consisting of a hydroxyl group, a carboxyl group, a carboxylate group, an optionally substituted heterocyclic group containing one or more nitrogen atoms, amino, alkylamino, dialkylamino, ammonium group, polyether radicals and polyetherester radicals.

4. The polyammonium/polysiloxane copolymer of claim 2, wherein R is at least one amine oxide group of the formula (IV):

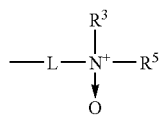

5. The polyammonium/polysiloxane copolymer of claim 2, wherein L is selected from $C_1$ to $C_{10}$-alkylene groups which may be linear, branched or cyclic.

6. The polyammonium/polysiloxane copolymer of claim 1, wherein the copolymer has at least two repeat units $V^2$.

7. The polyammonium/polysiloxane copolymer of claim 1, wherein V is $V^2$, and $V^2$ is a group of the following formula

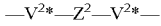

in which $Z^2$ is as defined above and $V^{2*}$ is a divalent straight-chain, cyclic or branched, saturated, unsaturated or aromatic hydrocarbon radical which has up to 40 carbon atoms and may optionally contain one or more groups selected from —O—, —NR$^2$—, —N$^+$R$^2{}_2$—, in which $R^2$ is as defined above, —C(O)— and —C(S)—, and the $V^{2*}$ radical may optionally be substituted by one or more hydroxyl groups.

8. The polyammonium/polysiloxane copolymer of claim 1, wherein V is $V^1$ and $V^1$ is selected from divalent, straight-chain, cyclic and branched, saturated, unsaturated and aromatic hydrocarbon radicals which have up to 600 carbon atoms and may optionally contain one or more groups selected from —O—, —NR$^2$—, —N$^+$R$^2{}_2$—, in which $R^2$ is as defined above, —C(O)—, —C(S)—, and —Z$^1$—, in which $Z^1$ is a group of the formula

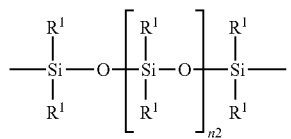

in which
$R^1$ is $C_1$ to $C_3$-alkyl, fluoro($C_3$-$C_6$)-alkyl or $C_6$-aryl, and $n_2$ is as defined above.

9. A compound of formula (V) or an acid addition salt thereof:

wherein groups R are independently organic groups which contain at least one selected from the group consisting of quaternary ammonium groups and amine oxide groups, wherein V is selected from a plurality of groups $V^1$ and a plurality of groups $V^2$, wherein the plurality of groups $V^1$ may be the same or different, and the plurality of groups $V^2$ maybe the same or different, in which $V^2$ is selected from divalent and trivalent, straight-chain, cyclic and branched, saturated, unsaturated and aromatic hydrocarbons including at least one $Z^2$ group of the formula

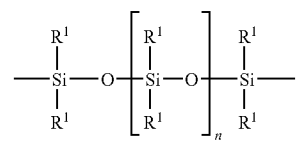

wherein groups $R^1$ may be the same or different and are selected from the group consisting of $C_1$-$C_{22}$ alkyl, fluoro ($C_1$-$C_{10}$) alkyl, and $C_6$-$C_{10}$ aryl, and wherein n1=20 to 1000, wherein $V^2$ includes up to 1000 carbon atoms exclusive of the $Z^2$ group and wherein $V^2$ may optionally contain one or more groups selected from
—OH,
—O—,
—NR$^2$—,
—N$^+$R$^2{}_2$—
  in which $R^2$ is hydrogen, a monovalent, straight-chain, cyclic or branched, saturated, unsaturated or aromatic hydrocarbon radical which has up to 100 carbon atoms and may contain one or more groups selected from —O—, —NH—, —C(O)— and —C(S)—, and which may optionally be substituted by one or more substituents selected from the group consisting of a hydroxyl group, an optionally substituted heterocyclic group containing one or more nitrogen atoms, amino, alkylamino, dialkylamino, polyether radicals and polyetherester radicals, where, when a plurality of —NR$^2$— groups is present, they may be the same or different,
—C(O)—,
—C(S)—
and
wherein $V^1$ is selected from divalent and trivalent, straight-chain, cyclic and branched, saturated, unsaturated and aromatic hydrocarbon radicals which have up to 1000 carbon atoms and may optionally contain one or more groups selected from
—OH,
—O—,
—NR$^2$—,
—N$^+$R$^2{}_2$—
  in which $R^2$ is as defined above, and where the $R^2$ groups in the $V^1$ and $V^2$ groups may be the same or different, —C(O)—,
—C(S)— and
—$Z^1$—, in which —$Z^1$— is a group of the formula
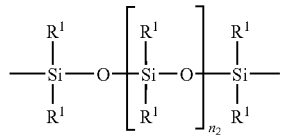
in which $R^1$ is as defined above, where the $R^1$ groups in the $V^1$ and $V^2$ groups may be the same or different,
$n_2$=0 to 19,
wherein acid anions neutralize the ammonium groups, and
with the proviso that V contains $Z^1$ or $Z^2$,
or an acid addition salt of $Z^2$.
10. The compound of claim 9, wherein V is $V^2$.
* * * * *